United States Patent [19]

Mann et al.

[11] Patent Number: 4,825,870
[45] Date of Patent: May 2, 1989

[54] PACEMAKER HAVING CROSSTALK PROTECTION FEATURE

[75] Inventors: Brian M. Mann, Los Angeles; Stuart W. Buchanan, Saugus, both of Calif.

[73] Assignee: Siemens-Pacesetter, Inc., Sylmar, Calif.

[21] Appl. No.: 64,899

[22] Filed: Jun. 19, 1987

[51] Int. Cl.[4] .................. A61N 1/00; H05G 00/00
[52] U.S. Cl. ......................................... 128/419 PG
[58] Field of Search .................. 128/419 PG, 419 P

[56] References Cited

U.S. PATENT DOCUMENTS

| | | | |
|---|---|---|---|
| 4,343,311 | 8/1982 | Markowitz | 128/419 PG |
| 4,407,287 | 10/1983 | Herpers | 128/419 PG |
| 4,412,541 | 11/1983 | Schaldach et al. | 128/419 PG |
| 4,429,697 | 2/1984 | Nappholz et al. | 128/419 PG |
| 4,452,248 | 6/1984 | Keller, Jr. | 128/419 PG |
| 4,462,406 | 7/1984 | DeCote, Jr. | 128/419 PG |
| 4,462,407 | 7/1984 | Herscovici et al. | 128/419 PG |
| 4,470,418 | 9/1984 | Herscovici et al. | 128/419 PG |
| 4,572,192 | 2/1986 | Jackman et al. | 128/419 PG |
| 4,586,507 | 5/1986 | Herscovici | 128/419 PG |
| 4,686,989 | 8/1987 | Smyth et al. | 128/419 PG |
| 4,714,079 | 12/1987 | Hedberg et al. | 128/419 PG |

OTHER PUBLICATIONS

Irnich, Werner, *Boston Colloguium on Cardiac Pacing*, 1977, p. 116 +.

Primary Examiner—Francis Jaworski
Assistant Examiner—George Manuel
Attorney, Agent, or Firm—Bryant R. Gold; Leslie S. Miller

[57] ABSTRACT

Programmable timing and logic circuitry is provided to detect crosstalk between paced chambers of the heart and to provide compensation in the event crosstalk is detected. Signals sensed during a prescribed time window early in the cardiac cycle following an atrial pulse are presumed to be crosstalk. If crosstalk occurs, a shortened AV delay is triggered. If crosstalk does not occur, a programmed AV delay is maintained. Absent the occurrence of a ventricular event after the prescribed time window up to the end of the AV delay, a ventricular stimulation pulse is provided. If a ventricular event is sensed during this time, the ventricular stimulation pulse is inhibited.

21 Claims, 3 Drawing Sheets

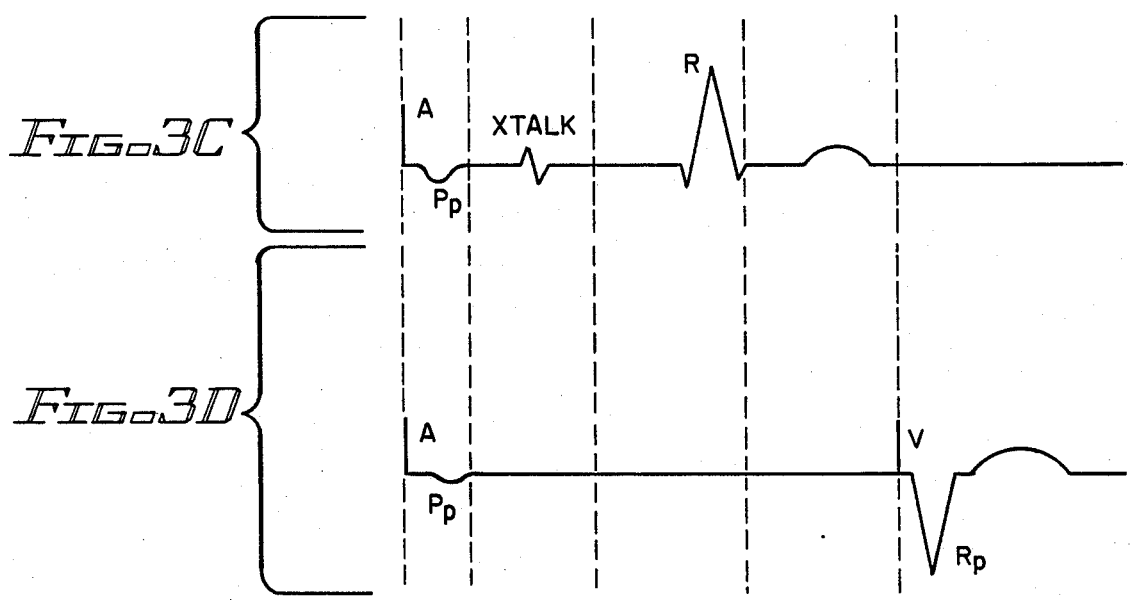
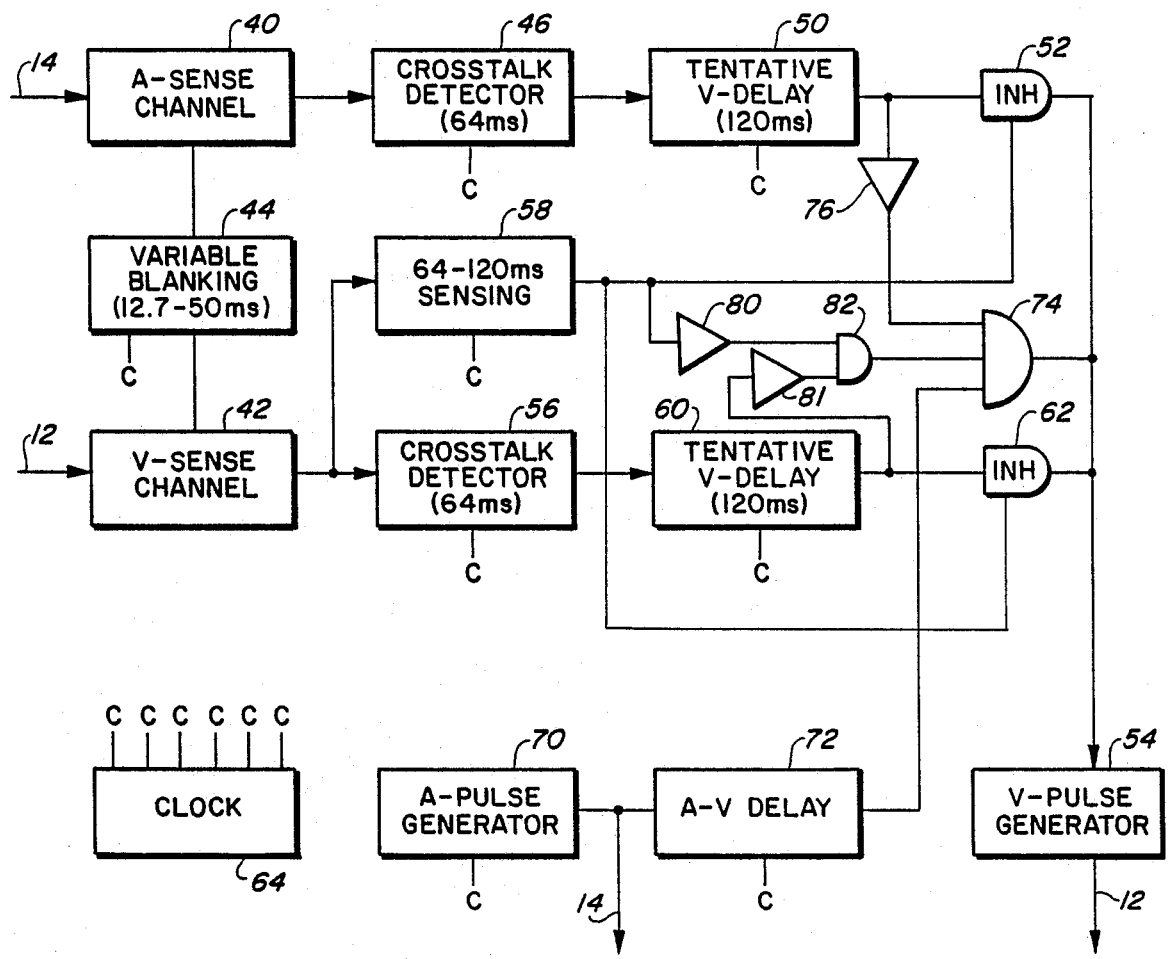

PACEMAKER HAVING CROSSTALK PROTECTION FEATURE

This invention relates to cardiac pacemakers and, more particularly, to an implantable, programmable, dual-chamber cardiac pacemaker having the capability of detecting crosstalk between atrial and ventricular activities and compensating for a misinterpretation of such crosstalk as activity within the heart chamber which is sensed.

BACKGROUND OF THE INVENTION

The technology of cardiac pacemakers has developed to a high level of sophistication of system performance. The current generation of cardiac pacemakers incorporate microprocessors and related circuitry to sense and stimulate heart activity under a variety of physiological conditions. These pacemakers may be programmed to control the heart in correcting or compensating for various heart abnormalities which may be encountered in individual patients. A detailed description of modern cardiac pacemaker technology is set forth in International Application No. PCT/US85/02010, entitled STIMULATED HEART INTERVAL MEASUREMENT, ADAPTIVE PACER AND METHOD OF OPERATION, assigned to the assignee hereof. The disclosure of that application is incorporated herein by reference.

In order to efficiently perform its function as a pump, the heart must maintain a natural AV synchrony. The term "AV synchrony" relates to the sequential timing relationship that exists between the contractions of the atria and the ventricles. In a given heart cycle or beat, these contractions are typically manifest or measured by sensing electrical signals or waves that are attendant with the depolarization of heart tissue, which depolarization immediately precedes (and for most purposes can be considered concurrent with) the contraction of the cardiac tissue. These signals or waves can be viewed on an electrocardiogram and include a P-wave, representing the depolarization of the atria; the QRS wave (sometimes referred to as an R-wave, the predominant wave of the group), representing the depolarization of the ventricles; and the T-wave, representing the repolarization of the ventricles. (It is noted that the atria also are repolarized, but this atrial repolarization occurs at approximately the same time as the depolarization of the ventricles; and any electrical signal generated by atrial repolarization is generally minute and is masked out by the much larger QRS-wave on the electrocardiogram.) Thus, it is the P-QRS-T cycle of waves that represents the natural AV synchrony of the heart. These waves, including the time relationships that exist therebetween, are carefully studied and monitored through conventional ECG techniques whenever the operation of the heart is being examined.

Multiple-mode, dual-chamber, demand-type, cardiac pacemakers are designed, insofar as possible, to maintain an AV synchrony for damaged or diseased hearts that are unable to do so on their own. This is realized by placing electrodes in both the right atrium and right ventricle of the heart. These electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing. This stimulation pulse causes or forces the desired depolarization and contraction of the indicated chamber to occur. Hence, by first sensing whether a natural depolarization occurs in each chamber, and by second stimulating at controlled time intervals each chamber with an external stimulation pulse in the absence of a natural depolarization, the AV synchrony of the heart can be maintained.

Unfortunately, there are many operating constraints and conditions of the heart that complicate the operation of a demand-type pacemaker. (A demand-type pacemaker is one that provides a stimulation pulse only when the heart fails to produce a natural depolarization on its own within a prescribed escape interval.) For example, there are certain the periods following a depolarization of cardiac tissue (prior to repolarization) when the application of an external electrical impulse is ineffective—that is, it serves no useful purpose, and thus represents an unneeded expenditure of the pacemaker's limited energy. Therefore the application of stimulation pulses during these time periods is to be avoided. Further, it is not uncommon for extraneous electrical signals or noise to be present. These electrical noise signals may be of sufficient amplitude to be sensed by the sensing amplifiers of the pacemaker, which sensing can "fool" the pacemaker into thinking that is has sensed electrical activity associated with a natural depolarization of the heart tissue, when in fact all that it has sensed is noise.

Where signals originating in one chamber of the heart are picked up and sensed by sensing circuits designed to sense signals in the other chamber of the heart, this particular noise problem is identified as "crosstalk." As a specific example, the atrial sense circuits may sense activity that occurs in the ventricle (also known as farfield sensing), or the ventricle sensing circuits may sense activity that occurs in the atrium (most common, and the main problem addressed by this invention). In either event, the pacemaker logic technically has no way to determine whether the sensed signal is a legitimate signal (one that should be acted upon in a prescribed manner) or a crosstalk signal (one that essentially represents noise and should not be acted upon as a legitimate signal).

While it should be noted that crosstalk can originate from several sources, for purposes of this application the most common source of crosstalk is the atrial stimulation pulse which is generated by the pacemaker being cross-coupled to the sensing circuits or electrode of the ventricular channel.

In order to prevent the pacemaker from generating and delivering stimulation pulses during the natural refractory time period of the heart, or from sensing and responding to electrical noise, it is common in the art to include within the pacemaker a timer circuit that defines a refractory period immediately subsequent to the sensing of major electrical activity, or immediately subsequent to the generating of an electrical stimulus. Pacemaker refractory periods have been used to block out noise for a prescribed time interval during a cardiac cycle. For example, during such a refractory period, the pacemaker sense amplifiers may be disabled for a first portion—the absolute refractory period—during which nothing can be sensed. During a second portion—the relative refractory period—the sense circuit can sense activity, but that which is sensed is usually considered to be noise.

Other methods are known in the art for specifically detecting or minimizing crosstalk or cross-coupling between heart chambers or the respective channel circuits or electrodes of the pacemaker. For example, U.S. Pat. No. 4,462,406 of DeCote, Jr. discloses the prevention of crosstalk between atrial and ventricular channels by multiplexing the atrial leads and ventricular leads at about 2 kHz, a rate which is well above the sense amplifier's upper frequency response.

U.S. Pat. No. 4,462,407 of Herscovici et al. prevents crosstalk between atrial and ventricular leads by using separate input/output circuits for the two channels which are powered by respective isolation capacitors. This arrangement is directed primarily to eliminating crosstalk originating within the pacemaker circuits.

U.S. Pat. No. 4,470,418 of Herscovici et al. reduces interchannel crosstalk in a dual-chamber pacemaker designed for bipolar leads by using a switching circuit that shunts an isolation resistance buffer amplifier in series with the lead electrodes during stimulation. This patent also discloses connecting a differential amplifier in series with a led during sensing, which amplifier is bypassed during pacing.

U.S. Pat. No. 4,586,507 of Herscovici prevents cross-stimulation, a related but not identical problem to crosstalk, between the atrium and ventricle leads during pacing by switchably connecting separate output capacitors in series with the respective leads, which capacitors are isolated from being charged in one channel until after a stimulus has been delivered on the other channel.

These examples of known prior art, while directed to the problem of crosstalk and similar problems, as is the present invention, all depend upon switching the applicable circuits on separate signal channels at different intervals during the heart pacing cycle. Dealing with the problem of crosstalk in such a manner adds to the complexity of the circuitry of the pacemaker, increases the circuit drain on the pacemaker power source, and may degrade pacemaker reliability.

SUMMARY OF THE INVENTION

In brief, pacemakers incorporating embodiments of the present invention serve to prevent inappropriate inhibition of the pacemaker's ventricular output if crosstalk is detected.

Pacemakers in accordance with the present invention provide an atrial to ventricular interval, or AVI, initialized by the generation of an A-pulse, following which a ventricular stimulus is generated unless an R-wave is previously detected. The AVI includes a blanking period, immediately following the atrial stimulation pulse, and a crosstalk detection window which follows the blanking period. In one particular embodiment, the blanking period and the crosstalk detection window together equal 64 milliseconds. For example, where the blanking period equals 25 milliseconds, the crosstalk detection window is 64 minus 25 or 39 milliseconds. Where the blanking period itself is programmable, as for example from 5 to 50 milliseconds, the duration of the crosstalk detection window equals 64 milliseconds minus the programmed blanking period.

During this crosstalk detection window, the sensing circuits of the pacemaker are operable to detect a signal which may be present. This may be a signal in one chamber corresponding to crosstalk from the other chamber, it may be a lingering portion of the atrial stimulation pulse in a case where the A pulse has not been fully damped by the end of the blanking period, or it may be interaction from one channel to another.

If any signal is sensed during the duration of the crosstalk detection window, the pacemaker sets its AVI to 120 ms, thereby causing the pacemaker to deliver a ventricular output 120 ms after the atrial stimulation pulse which initiates the timing of the pacing cycle. If no signal is sensed during the crosstalk detection window, the pacemaker keeps its AVI set to a programmed value (which can be greater than 120 ms), thereby causing a ventricular output pulse to be delivered at the end of the programmed AVI. However, in either case, normal sensing is maintained following the termination of the crosstalk detection window up to the end of the AVI. If, during this interval of normal sensing beginning after the 64 ms termination of the crosstalk detection window and continuing to the end of the AVI (which AVI may end at 120 ms or a programmed value, depending upon whether any signals were sensed during the crosstalk detection window) a ventricular event is sensed, the pacemaker inhibits the ventricular stimulation pulse. In other words, if a normal ventricular depolarization is sensed, even if crosstalk is detected during the crosstalk detection window interval, the ventricular stimulation signal does not occur. Thus, the pacemaker in accordance with the present invention monitors the heart to detect crosstalk, defined as any signals sensed within a predetermined interval following the atrial stimulation pulse. If crosstalk is detected, the pacemaker follows with a ventricular stimulation pulse at the end of the AVI (which AVI assumes one of two values depending upon whether crosstalk was detected) following the atrial pulse unless a normal ventricular activity is sensed, in which case the ventricular stimulation pulse is inhibited.

BRIEF DESCRIPTION OF THE DRAWINGS

The above and other objects, features and advantages of the present invention will be more apparent from the following more particular description thereof presented in conjunction with the accompanying drawings, wherein:

FIGS. 3A–D are a set of waveforms and timing intervals representative of the pacemaker of FIG. 1 operating in accordance with the present invention;

FIG. 5 is a block diagram representing circuitry of a different embodiment of the present invention.

DETAILED DESCRIPTION OF THE INVENTION

The following description is of the best presently contemplated mode of carrying out the invention. This description is not to be taken in a limiting sense but is made for the purpose of describing the general principles of the invention. The scope of the invention should be determined with reference to the appended claims.

Figure 1:
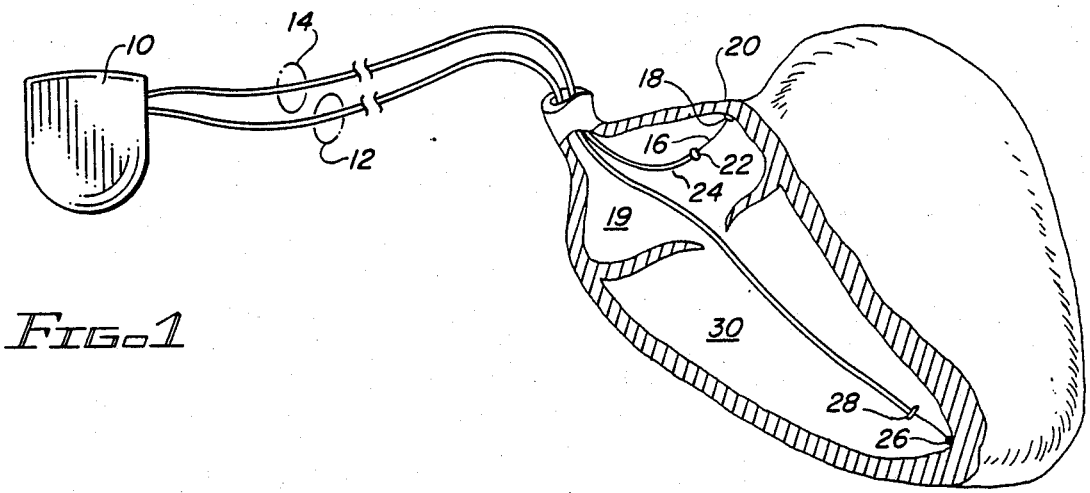
FIG. 1 is a schematic representation of a dual-chamber cardiac pacemaker installed in association with a heart for pacing.

Referring now to FIG. 1, there is shown a simplified representation of one way that an implanted pacemaker 10 may make electrical contact with the heart. FIG. 1 depicts the use of two bipolar leads 12 and 14, each being directed into a separate chamber of the right heart. A bipolar lead comprises a single filar that includes two electrically insulated conductors. For example, the lead 14 includes a first conductor 16 that is electrically connected to a distal tip 18 of the lead. This distal tip is typically placed in a cavity of the right atrium 19 referred to as the atrial appendage 20. A known distance from the distal tip 18 an electrode ring 22 is electrically connected to the other conductor 24 of the bipolar lead 14. Similarly, a distal tip 26 and a conductive ring 28 are associated with the bipolar lead 12 that is placed in the apex of the right ventricle 30. The manner in which the leads 12 and 14 are inserted into the heart, as well as the manner in which the pacemaker 10 is implanted in the body of a patient, are well known in the art.

Figure 2:
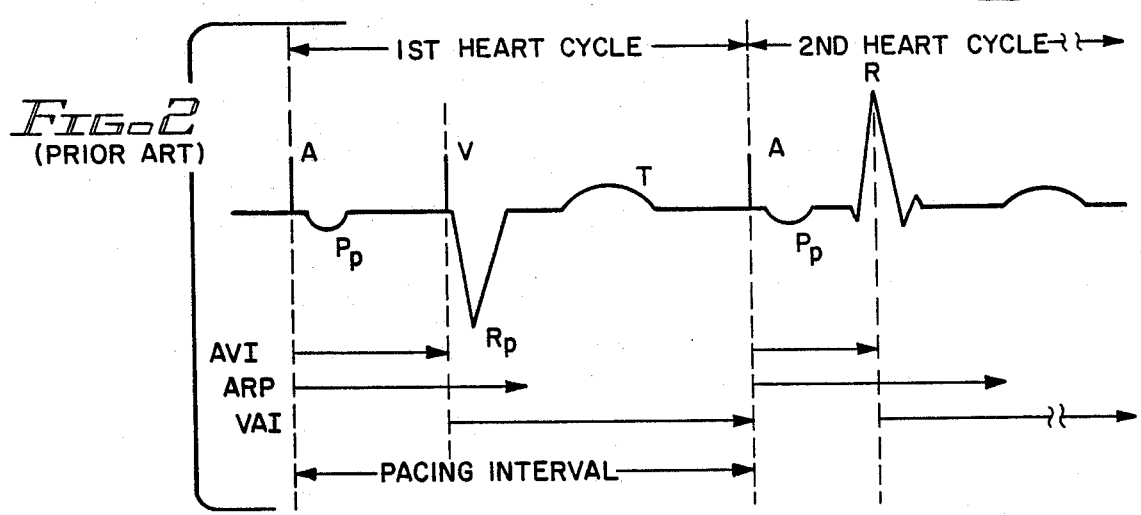
FIG. 2 is a waveform representing heart action in association with pacing.

FIG. 2 shows a timing diagram which illustrates the response of the heart to stimulation pulses that are generated by an implanted pacemaker, such as the pacemaker 10 shown in FIG. 1. The timing diagram of FIG. 2 defines various intervals that are commonly used in controlling a dual-chamber demand-type pacemaker. In a pacemaker of this type, it is common to define an escape interval during which activity within the heart is sensed. If a natural cardiac event occurs during this escape interval—i.e., if a natural P-wave or R-wave is sensed, then a corresponding stimulating pulse need not be generated. Not only does this mode of operation allow the heart to function in its natural state, if it is able, but it also helps conserve the limited power stored within the battery of the pacemaker. In response to an atrial stimulation pulse, or A-pulse, delivered to the right atrium 19 through the distal tip 20 of lead 14 (FIG. 1), both atria contract and a P-wave is generated. Because the stimulating A-pulse originates from a different point within the right atrium than does the normal stimulating pulse of the heart, the P-wave generated in response to this A-pulse does not appear the same as a naturally occurring P-wave. For purposes of this application, this difference between a P-wave in response to an A-pulse and a P-wave in response to the naturally occurring pulse of the heart is depicted as a P-wave of opposite polarity. The waveform of FIG. 2 is further distinguished by referring to it as the $P_P$-wave, indicating that it is a paced P-wave, or a P-wave in response to a pacing signal.

Similarly, in response to a stimulation pulse applied to the right ventricle, an R-wave is generated, represented in FIG. 2 as an inverted $R_p$-pulse. The R-wave in FIG. 2 is shown inverted from the R-wave to the right of the figure because the stimulating pulse propagates through the ventricle chamber in a different direction than does the natural stimulating pulse that propagates through the left and right ventricle signal paths. Hence for purposes of this application, the natural responses or natural depolarizations of the heart are represented in the figures as a positive P-wave (a waveform going in the upwards direction) and a positive R-wave. Depolarization of the atria or ventricles in response to an externally generated stimulation pulse, such as the A-pulse or V-pulse of the pacemaker, are represented as a negative going $P_p$-wave or $R_p$.

The atrial escape interval is represented in FIG. 2 as VAI. This is a prescribed time set by the pacemaker during which a naturally occurring P-wave must occur, if one is to occur, prior to the generation of an atrial stimulation pulse, or A-pulse. Similarly, a naturally occurring R-wave must occur, if one is to occur, prior to the termination of the AV interval, or AVI. As indicated in FIG. 2 for the first heart cycle portion of the waveform, the AVI has timed out, thereby causing the V-pulse to be generated. During the second heart cycle, however, AVI has not yet timed out at the point in time when the naturally occurring R-wave appears. Thus there is no need for the pacemaker to generate a V-pulse during the second heart cycle.

Also illustrated in FIG. 2 is an atrial refractory period, ARP. During this refractory period, the normal sensing mechanisms used within the atrium are non-responsive. This refractory period is analogous to the natural refractory period of myocardial tissue immediately following depolarization and prevents the pacemaker from detecting any polarization signals or noise that might result in timing errors.

The VA interval, or VAI, of FIG. 2 is initiated by the generation of a V-pulse, or the sensing of a natural R-wave. This VA interval, less the atrial refractory period, ARP, defines the time during which a natural (non-paced) P-wave must be detected if the atrial stimulation pulse is to be inhibited. In FIG. 2, the pacing interval or rate set by the pacemaker is equal to the VA interval, VAI, plus the AV interval, AVI. Controlling the duration of these two time periods, AVI and VAI, either together or relative to each other, is a common approach to controlling the pacing interval of the pacemaker and thereby the heart rate.

Figure 3A:
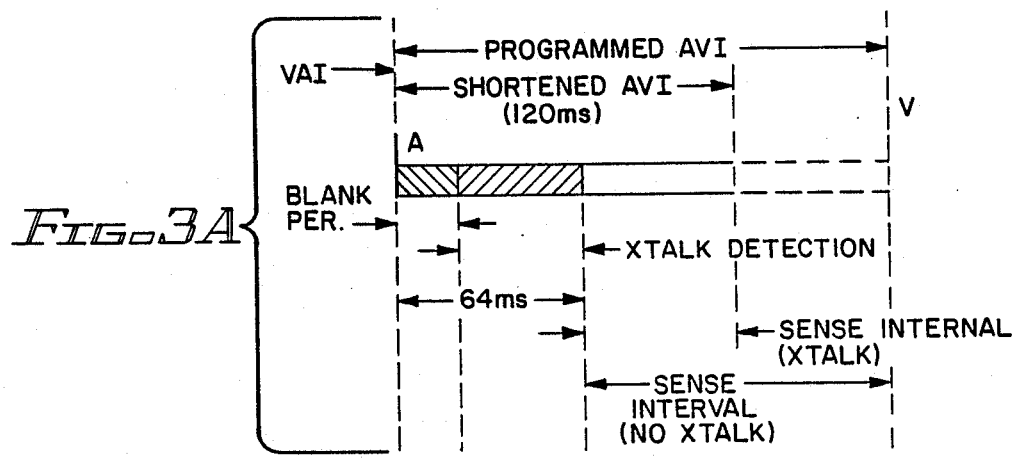

In accordance with the present invention, the pacemaker 10 of FIG. 1 as described hereinabove is modified to operate as indicated by the waveform and timing diagrams of FIGS. 3A–3D. Referring to FIG. 3A, various timing intervals are defined that relate to the present invention. The timing out of the atrial escape interval, VAI, causes the generation of an A-pulse, which A-pulse is followed by the AV interval, AVI. The AVI may assume one of two values: (1) a programmed value, or (2) a shortened value. In the preferred embodiment, the shortened value is 120 ms and is used as the AVI only when crosstalk is detected. A V-pulse follows the timing out of the AVI if required, i.e., if no R-wave is previously sensed, as described below. The principal function of this embodiment of the present invention is to prevent the inappropriate inhibition of the pacer's ventricular output if crosstalk occurs. This embodiment of the invention divides the AVI into three subintervals: (1) a blanking period; (2) a crosstalk detection window; and (3) a sense interval. The blanking period immediately follows an A-pulse. In one embodiment, this blanking period is programmably settable in four steps: 13 ms, 25 ms, 38 ms or 50 ms. During this blanking period, all sensing is disabled. After termination of the blanking period, the crosstalk detection window is initiated which extends until 64 ms following the A-pulse. During the crosstalk detection window, the pacemaker pulse generating circuits are disabled, but sensing occurs. If any signal is sensed during the crosstalk detection window, the pacer 10 (FIG. 1) sets AVI to 120 ms, thereby readying the pacer to deliver a ventricular output 120 ms after the atrial output. If no signal is sensed during the crosstalk detection window, AVI remains set at its programmed value (which programmed value can be greater than 120 ms). Following the crosstalk detection window comes a sense interval.

The sense interval lasts until the end of the AVI. If crosstalk has been detected, the sense interval thus covers the time from 64 ms after the A-pulse (at the conclusion of the crosstalk detection window) to 120 ms (the end of the shortened AVI). If no crosstalk has been detected, the sense interval covers the time from 64 ms after the A-pulse to the end of the programmed AVI. During the sense interval, normal sensing is maintained. If a ventricular event is sensed within this sensing interval, the ventricular output is inhibited, even though crosstalk may have been detected during the crosstalk detection window. Detecting crosstalk thus alters the length of the AVI; it does not alter the function of the sense interval.

Figure 3B:
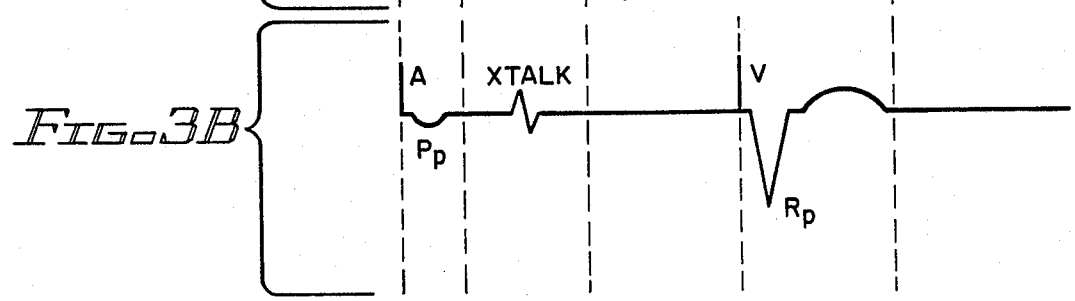

FIG. 3B illustrates what happens when crosstalk is detected during the crosstalk detection window and no ventricular events are sensed during the sense interval—a V-pulse is delivered 120 ms after the A-pulse. FIG. 3C similarly illustrates what happens when crosstalk is detected during the crosstalk detection window and an R-wave is sensed during the sense interval—no V-pulse is generated. Finally, FIG. 3D shows what happens when no crosstalk is detected during the crosstalk detection window—the AVI remains at its programmed value. Further, FIG. 3D illustrates the situation where no ventricular event is sensed during the sense interval following the crosstalk detection window.

Figure 4:
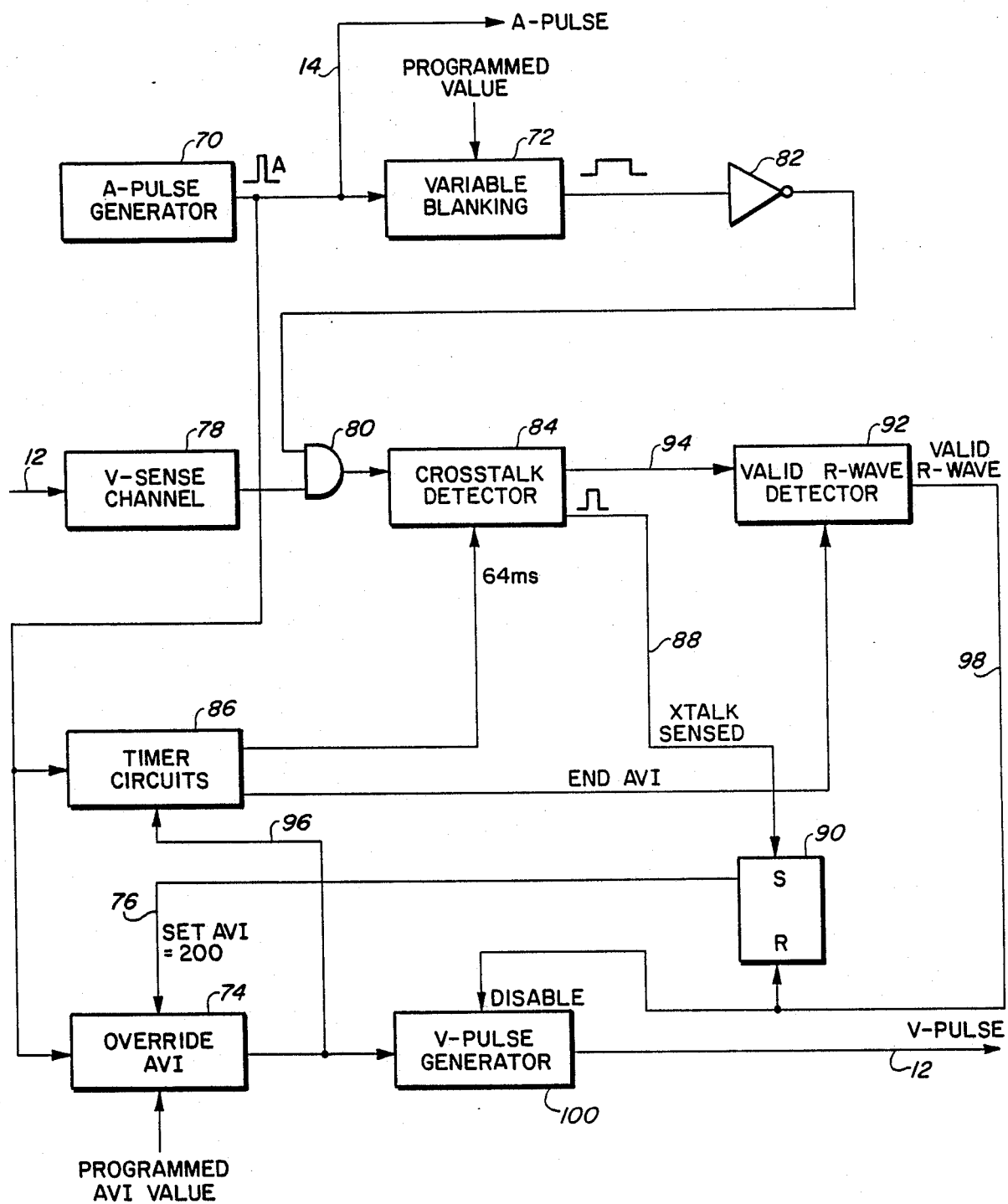
FIG. 4 is a block diagram representing circuitry of a preferred embodiment of the present invention.

The block diagram of FIG. 4 represents timing and logic circuitry embodying the present invention. That is, the circuitry shown in FIG. 4 is used to realize the results shown in FIGS. 3A-3D. It is noted that FIG. 4 represents a simplified block diagram that incorporates only those elements required to practice the present invention. The figure is drawn depicting these elements as separate elements that could be added to the conventional circuits of a dual chamber pacemaker, which conventional circuits are well known in the art and are thus not duplicated here. It should be noted, however, that while FIG. 4 has been drawn so as to clearly teach the operating principles and basic structure required to practice the present invention, many of the functions performed by the elements shown in FIG. 4 could readily be incorporated within the already existing elements of a dual chamber pacemaker by those skilled in art.

Referring then to FIG. 4 it is seen that the present invention includes an A-pulse generator 70, which generator 70 is the same generator used by the conventional pacemaker circuits to generate an A-pulse and deliver it to the heart over the pacer lead 14. As is known to those skilled in the art, there are conditions defined within the logic of a dual chamber pacemaker that cause an A-pulse to be generated. For purposes of the present invention, it matters only that an A-pulse has been generated. Hence, the conditions that cause the A-pulse to be generated are not shown in FIG. 4.

The generation of an A-pulse triggers variable blanking circuit 72 and AVI circuit 74. Variable blanking circuit 72 generates the blanking period, shown in FIG. 3A. This period is programmable, and will typically be programmed to assume a value of between 5 and 50 msec. In one embodiment, it is programmed to be approximately 13, 25, 38 or 50 ms. AVI circuit 74 generates the AV interval (AVI) shown in FIG. 3A. As previously indicated, the AVI may assume one of two values: a programmed value (such as 230 ms), or a shortened value equal to 120 ms. The length of the AVI is controlled by a control signal received over signal line 76, as described below.

Still referring to FIG. 4, it is seen that V-Sense Channel circuit 78 is coupled to receive sensed signals from the ventricle of the heart over ventricular lead 12. The output of V-Sense Channel 78 is directed to functional AND gate 80 where it is gated with the inverted output (inverted by INVERTER gate 82) from blanking circuit 72. Thus, only signals sensed by V-sense Channel 78 that occur after the blanking period defined by the blanking circuit 72 are allowed to pass through AND gate 80.

Signals passing through AND gate 80 are coupled to Crosstalk Detector 84. It is the function of Crosstalk Detector 84 to detect all signals occurring within the time interval beginning immediately after termination of the blanking period up to 64 ms after the generation of the A-pulse. That is, it is the function of the Crosstalk Detector 84 to detect all signals occurring within the crosstalk detection window. A 64 ms reference signal used to define the end of the crosstalk detection window is provided to Crosstalk Detector 84 from the timer circuits 86, which circuits 86 are also initialized by the generation of the A-pulse.

If Crosstalk Detector 84 determines that a signal has occurred within the crosstalk detection window, a "XTALK SENSED" signal is generated on signal line 88. This signal sets latch 90, which latch provides the control signal on signal line 76 that is directed to the AVI circuit 74. In response to the setting of latch 90, AVI circuit 74 selects the AV interval to be 120 ms. (the shortened AVI shown in FIG. 3A) instead of the programmed value of AVI. This shortened AVI will be generated by AVI circuit 74 for use only within the cardiac cycle initiated by the most recently generated A-pulse. At all other times, the programmed value of AVI will be generated.

Regardless of whether or not the Crosstalk Detector 84 determines that crosstalk occurred during the crosstalk detection window, any signals sensed by V-sense Channel circuit 78 that occur during the sense period (FIG. 3A)—after the termination of the crosstalk detection window and prior to the termination of the AVI—are sensed by Valid R-wave Detector 92 and deemed to be valid R-waves. The detection of a valid R-wave during the sense period causes a signal, VALID R-WAVE, to be generated on signal line 98. This signal is directed to V-pulse generator 100 and is used to disable the generation of the V-pulse for the current cycle. This signal also resets latch 90, and thus ensures that the AVI circuit 74 reverts to the programmed AVI value for the subsequent heart cycle.

The R-wave Detector 92 defines the sense interval, and hence is able to signal a valid R-wave (which is any signal that occurs during the sense interval) as follows: All signals that occur after the crosstalk detection window are passed through Crosstalk Detector 84 to the R-wave Detector 92 over signal line 94. The end of the AVI is indicated to the R-wave Detector 92 by a signal "END AVI" generated by the timer circuits 86. The timer circuits 86, in turn, monitor the current value of AVI (which can be either 120 ms or the programmed value) over signal line 96, which line is coupled to the output of the AVI circuit 74. Thus, any signal occurring after 64 ms. and prior to END AVI is categorized as a valid R-wave by R-wave Detector 92.

In operation, V-pulse generator 100 generates a V-pulse at the conclusion of the AVI unless the V-pulse generator is disabled. Disabling of the V-Pulse generator 100 occurs whenever a valid R-wave is detected within the sense interval. The sense interval is defined by the R-wave detector 92 as that period of time following the conclusion of the crosstalk detection window (which occurs 64 ms after the generation of the A-pulse) and the end of the AVI. The AVI may assume one of two values. If a signal is detected during the crosstalk detection window (which is the time interval following the blanking period up to 64 ms), the AVI is set at 120 ms. If no crosstalk is detected during the crosstalk detection window, the AVI is set to the programmed value. In this manner, the pacemaker in accordance with the present invention prevents inappropriate inhibition of the pacemaker's ventricular output (the V-pulse) if crosstalk is detected.

The block diagram of FIG. 5 schematically represents timing and logic circuitry embodying a different embodiment of the present invention. In FIG. 5, an A-sense channel 40 and V-sense channel 42 are shown coupled to receive sensed signals from the atrium and ventricle of the heart over respective leads 14 and 12. Both of these two sensing channels are coupled to a variable blanking stage 44 which can be set at a selected blanking interval to prevent any sensing in the two sensing channels 40, 42 during the selected intervals of 12.7 to 50 ms.

In the A channel, the output of the stage 40 is coupled to a crosstalk detector 46. The crosstalk detector 26 is set to provide a crosstalk detection window of 64 ms following the A-pulse which initiates timing for the cycle and can only be effective after the input channel 40 is no longer blanked by the stage 44. The output of the crosstalk detector 46 is coupled to a tentative V-delay stage 50 which is set to develop an output signal at 120 ms if it receives a signal from the crosstalk detector 46. At the output of the stage 50 is an inhibiting gate 52 which is connected to be controlled by an output from a sensing stage 58 in the V channel. The output of the inhibiting gate 52 is connected to the input of a V-pulse generator 54. With the A sensing portion of the system as thus described, a tentative V-delay signal is generated by the stage 50 if the crosstalk detector 46 receives any input within 64 ms before the A-pulse. Unless inhibited at the gate 52, the signal from the stage 50 will trigger the V-pulse generator 54 to send a pacing signal to the ventricle.

Still referring to FIG. 5, the V channel includes corresponding crosstalk detector stage 56, tentative V-delay stage 60 and inhibiting gate 62 with the addition of a normal sensing stage 58. The V-channel operates in like fashion to the A-channel in the detection of crosstalk from the opposite chamber of the heart to cause the generation of a V-pulse from the generator 54 if crosstalk is detected by the stage 56, absent normal heart activity within the interval from 64 to 120 ms following the A-pulse. If the normal sensing stage 58 detects a signal within the interval from 64 to 120 ms following the atrial pacing pulse, signifying normal heart activity in that interval, it inhibits both gates 52, 62, thereby blocking any trigger signal from the stages 50, 60. All of the timing circuits of FIG. 4 are coupled to a clock timer 64, as indicated by the leads marked "c".

The block diagram of FIG. 5 also includes circuitry to trigger the V-pulse generator 54 after a customary AV delay in the event that the crosstalk detector circuit portion does not trigger a V-pulse and there is no normal ventricle activity. This is represented by an A-pulse generator 70 coupled to an AV delay stage 72, the output of which is applied to an AND gate 74. In addition to the connections as thus far described, the output of the stage 50 is applied by inverter stage 76 to an AND gate 74. Similarly, outputs of the stages 58, 60 are applied by respective inverting blocks 80, 81 to an AND gate 82, the output of which is applied to the AND gate 74. With this circuit, if no signal appears on any output of the stages 50, 58 and 60, signifying a condition where a V-pulse is needed following the standard AV delay, the signal from the pulse generator 70, delayed by the AV delay stage 72, is fed through the enabled gate 74 to activate the V-pulse generator 54.

Thus arrangements in accordance with the present invention provide a particular modification of conventional AV pacing to compensate for the detection of crosstalk within a predetermined interval following the atrial pulse. As a result, a ventricular pulse is supplied at a fixed interval following the atrial pulse unless a normal ventricular event occurs, in which case, the ventricular pulse is unnecessary and is therefore dispensed with.

Although there have been described above specific arrangements of a pacemaker having crosstalk protection feature in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A cardiac pacing system comprising:

a dual-chamber cardiac pacemaker having leads for installation in an atrium and ventricle, respectively, each lead being adapted to both pick up electrical signals within the heart and to transmit pulses to stimulate heart activity within the associated heart chamber;

electrical circuitry coupled to at least one of said leads for sensing electrical signals picked up by said at least one lead and for generating stimulating signals under predetermined conditions;

timing means coupled to said electrical circuitry for timing the operation thereof;

an atrial pulse generator responsive to said timing means to provide an atrial pacing pulse; and a ventricular pulse generator for providing a ventricular output pulse in response to an applied triggering signal;

said electrical circuitry including:

a sense stage coupled to at least one of said leads for sensing signals thereon;

a crosstalk detector coupled to the sense stage for providing a control signal in the event a heart signal is sensed by the sense stage within a first predetermined interval following an atrial pacing pulse;

a tentative signal generator responsive to the crosstalk detector control signal for developing a signal to trigger the ventricular pulse generator at the end of a predetermined delay following and atrial pacing pulse;

a normal sensing stage coupled to sense ventricular depolarization and provide an inhibit signal in the event normal heart activity is sensed within a second predetermined interval following said first predetermined interval; and means responsive to said inhibit signal for inhibiting the trigger signal of the tentative signal generator.

2. The system of claim 1 further including a variable blanking stage coupled to the sense stage for blanking said stage during a selected blanking interval immediately following an atrial pacing pulse.

3. The system of claim 2 wherein said variable blanking stage is programmable to select one of a plurality of preset time periods for said blanking interval, each of said time periods being less than said first predetermined interval.

4. The system of claim 3 wherein said preset time periods comprise approximately 13, 25, 38 or 50 ms, wherein the first predetermined interval is 64 ms, wherein the second predetermined interval begins at the termination of said first predetermined interval and ends at 120 ms after the atrial pacing pulse, and wherein the predetermined delay of the tentative signal generator is 120 ms.

5. The system of claim 1 further including additional electrical circuitry coupled to the other of said leads, said additional electrical circuitry including a second sense stage, a second crosstalk detector, a second tentative signal generator, and second inhibiting means coupled to control the atrial pulse generator in the same manner as the previously described sense stage, crosstalk detector, tentative signal generator, and inhibiting means control the ventricular pulse generator.

6. The system of claim 5 further including a variable blanking stage programmable to select one of a plurality of preset blanking periods, said variable blanking stage being coupled to both the sense stage and second sense stage to blank said stages for the selected preset blanking period.

7. The system of claim 1 further including means for triggering the ventricular pulse generator from the atrial pulse generator in the event that no triggering pulse is provided by either channel and normal ventricular depolarization is not sensed.

8. The system of claim 7 comprising an Av delay stage coupled to the atrial pulse generator and gating means for applying a delayed signal from the Av delay stage to trigger the ventricular pulse generator only in the event that neither crosstalk nor normal ventricular activity is detected in either channel within a normal AV interval.

9. A crosstalk detection circuit for a cardiac pacemaker, said cardiac pacemaker having atrial and ventricular pulse generators for pacing a heart with which the pacemaker is associated, said pacemaker further having leads for installation in an atrium and ventricle respectively, each lead being adapted to both pick up electrical signals within the heart and to transmit pulses to stimulate heart activity within the associated heart chamber, said crosstalk detection circuit comprising:
a sense stage coupled to at least one of said leads for sensing signals thereon;
a crosstalk detector coupled to the sense stage for providing a control signal in the event a heart signal is sensed by the sense stage within a first predetermined interval following an atrial pacing pulse;
a tentative signal generator responsive to the crosstalk detector control signal for developing a signal to trigger the ventricular pulse generator at the end of a predetermined delay following an atrial pacing pulse;
a normal sensing stage coupled to sense ventricular depolarization and provide an inhibit signal in the event normal heart activity is sensed within a second predetermined interval following said first predetermined interval;
means responsive to said inhibit signal for inhibiting the trigger signal of the tentative signal generator; and
timing means for timing the operation of the circuit relative to an atrial pacing pulse.

10. The crosstalk detection circuit of claim 9 further including a variable blanking stage coupled to the sense stage for blanking said stage during a selected blanking interval immediately following an atrial pacing pulse.

11. The crosstalk detection circuit of claim 9 comprising pairs of sense stages, crosstalk detectors, tentative signal generators, and inhibiting means interconnected as defined in respective A- and V-channels, the V-channel including the normal sensing stage; and
means for coupling the output of each channel to the ventricular pulse generator to provide control of the ventricular pulse generator from either channel.

12. The method of controlling the triggering of a ventricular pulse generator of a dual-chamber cardiac pacemaker having connections to leads inserted, respectively, into an atrium and ventricle of a heart comprising the steps of:
sensing electrical signals within respective heart chambers during predetermined intervals following an atrial pacing pulse;
detecting crosstalk within a first predetermined interval following the atrial pacing pulse;
generating a signal to trigger the ventricular pulse generator with a predetermined delay following the atrial pacing pulse if crosstalk is detected;
monitoring the heart of normal ventricular activity and inhibiting said trigger signal in the event that normal ventricular activity is detected.

13. The method of claim 12 further including the step of blanking monitoring of the heart for a selected blanking period immediately following the atrial pulse and prior to said first predetermined interval for crosstalk detection.

14. The method of claim 12 wherein the step of detecting crosstalk includes detecting crosstalk in both heart chambers being sensed.

15. The method of claim 14 further including triggering the ventricular pulse generator after a predetermined AV interval in the absence of crosstalk and if normal ventricular activity is not sensed.

16. A crosstalk detection circuit for a cardiac pacemaker, said cardiac pacemaker having atrial and ventricular pulse generators for pacing a heart with which the pacemaker is associated, said pacemaker further having lead means for making electrical contact with said heart, said crosstalk detection circuit comprising:
sensing means coupled to said lead means for sensing signals thereon;
timing means for defining first and second time intervals, said first time interval beginning with the generation of an atrial stimulation pulse by aid atrial pulse generator, and said second time interval beginning at the conclusion of said first time interval;

crosstalk detection means coupled to said sensing means and said timing means for first determining if a signal is sensed within said first time interval and for generating a crosstalk signal in response to said first determination and for secondly determining if a signal is sensed by said sensing means during said second time interval and for generating an R-wave signal in response to said second determination;

adjustment means coupled to said timing means for automatically adjusting the length of said second time interval in response to the occurrence of said crosstalk signal; and control means coupled to said timing and detection means for causing said ventricular pulse generator to generate a ventricular stimulation pulse at the conclusion of said second time interval unless said R-wave signal occurs, said control means thereby inhibiting the generation of a ventricular stimulation pulse in response to the occurrence of said R-wave signal.

17. The crosstalk detection circuit of claim 16 wherein said first time interval generated by said timing means is further divided into a first time period and a second time period, and further wherein said detection means generates said crosstalk signal only if a signal is sensed within the second time period of said first time interval.

18. The crosstalk detection circuit of claim 17 wherein said first time period of said first time interval comprises a blanking period during which said sensing means is prevented from sensing any signals, and further wherein said second time period of said first time interval comprises a crosstalk detection window during which said sensing means is allowed to sense signals on said lead means, the sensing of any signals during said crosstalk detection window causing said crosstalk signal to be generated.

19. The crosstalk detection circuit of claim 18 wherein said timing means includes programming means for allowing the length of said blanking period to be programmably selected to a desired value within the range of 0 to 50 milliseconds.

20. The crosstalk detection circuit of claim 19 wherein said first time interval comprises a fixed time period greater than 60 milliseconds, whereby said crosstalk detection window assumes a value equal to this fixed time period less the blanking period.

21. The crosstalk detection circuit of claim 20 wherein said adjustment means adjusts the length of said second time interval in response to the occurrence of said crosstalk signal to a value of between 50 and 60 milliseconds.

* * * * *